(12) United States Patent
Zaiki

(10) Patent No.: US 7,577,237 B2
(45) Date of Patent: Aug. 18, 2009

(54) X-RAY IMAGING APPARATUS

(75) Inventor: Ryuji Zaiki, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/949,546

(22) Filed: Dec. 3, 2007

(65) Prior Publication Data
US 2008/0260103 A1   Oct. 23, 2008

(30) Foreign Application Priority Data
Dec. 18, 2006   (JP) ............................. 2006-340087

(51) Int. Cl.
G21K 1/04   (2006.01)
H05G 1/00   (2006.01)

(52) U.S. Cl. ....................... 378/150; 378/208

(58) Field of Classification Search ................ 378/4, 378/19, 20, 16, 147–153, 208, 209
See application file for complete search history.

(56) References Cited

U.S. PATENT DOCUMENTS 5,734,692 A * 3/1998 Seki ............................. 378/65
7,016,455 B2 * 3/2006 Bruder et al. ................. 378/9
2001/0019599 A1 * 9/2001 Guendel ....................... 378/15

* cited by examiner

Primary Examiner—Irakli Kiknadze
(74) Attorney, Agent, or Firm—Oblon, Spivak, McClelland, Maier & Neustadt, P.C.

(57) ABSTRACT

When a tabletop is rolling, an aperture specifying unit calculates an aperture of diaphragm blades such that a radiation field is to be R' based on a rolling angle, where R' is a radiation field having the same radiation area of X-rays after tabletop rolling as a radiation area before the tabletop rolling. The aperture specifying unit instructs a beam-limit control unit to take the calculated aperture of the diaphragm blades in an X-ray beam limiting device. Then, the beam-limit control unit controls the aperture of the diaphragm blades such that the radiation field is to be R'.

8 Claims, 11 Drawing Sheets

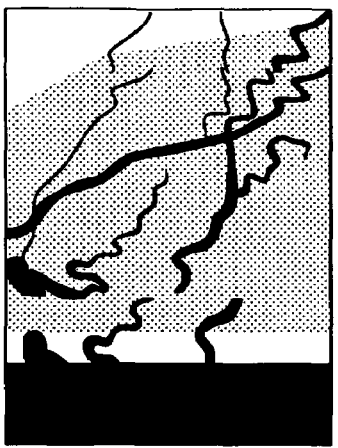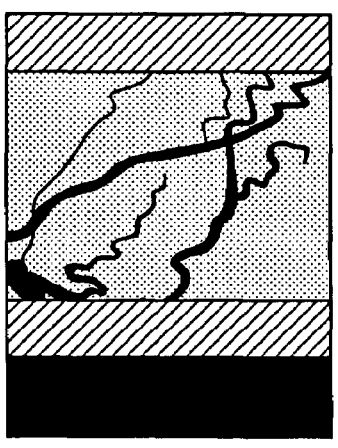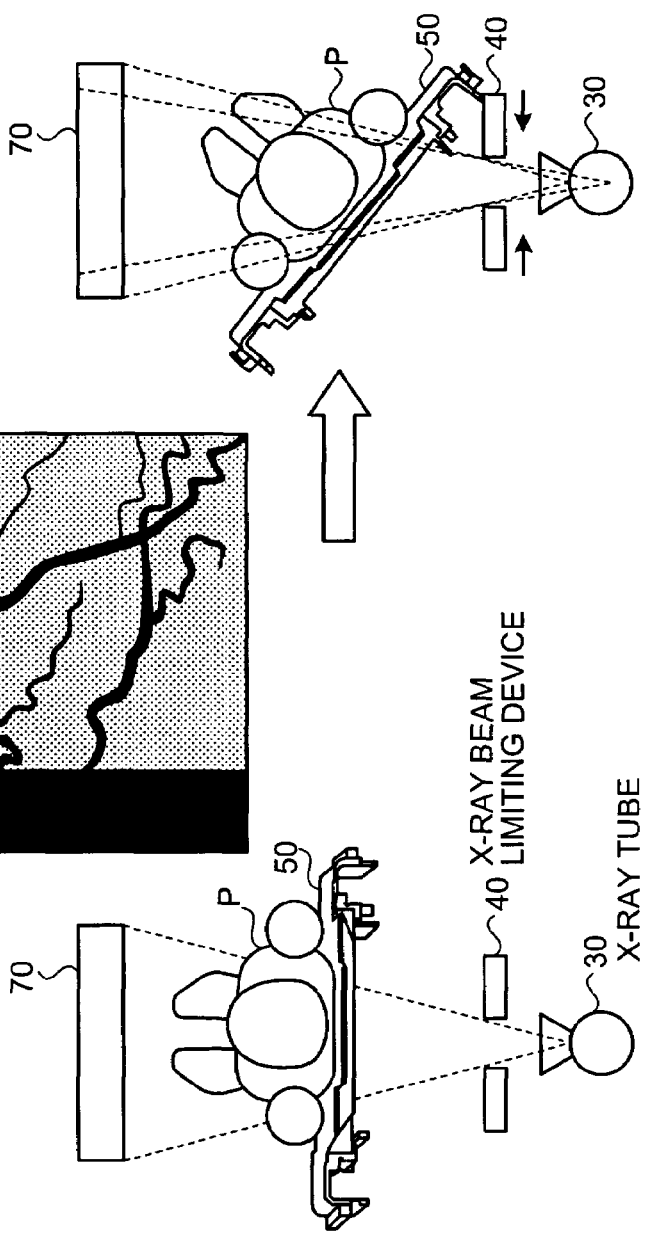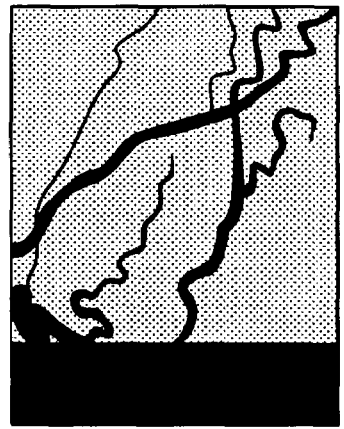

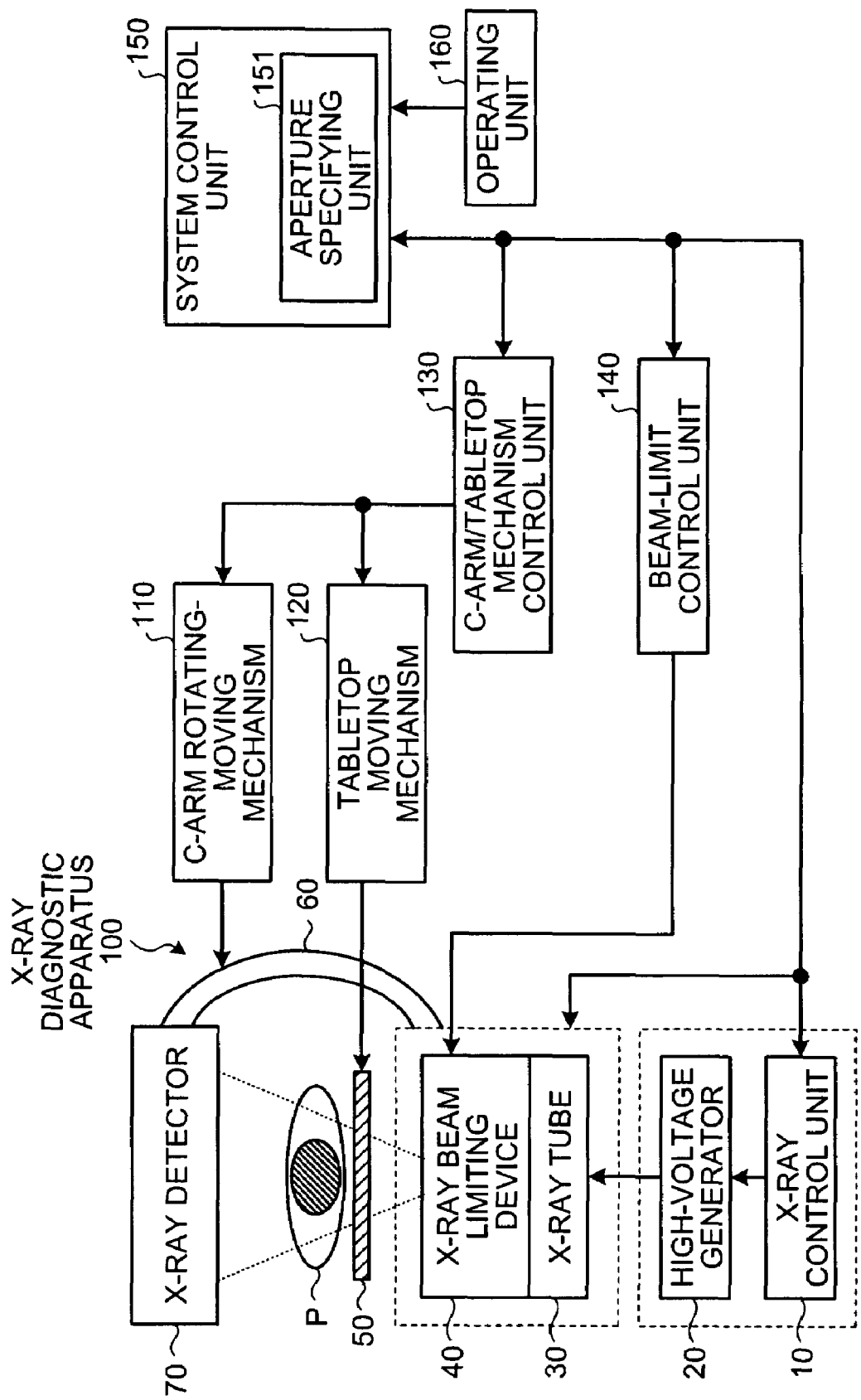

$R' = r_1 \times \cos(\beta_2 - \beta_1) + r_2 \times \cos(\beta_2 - \beta_1)$

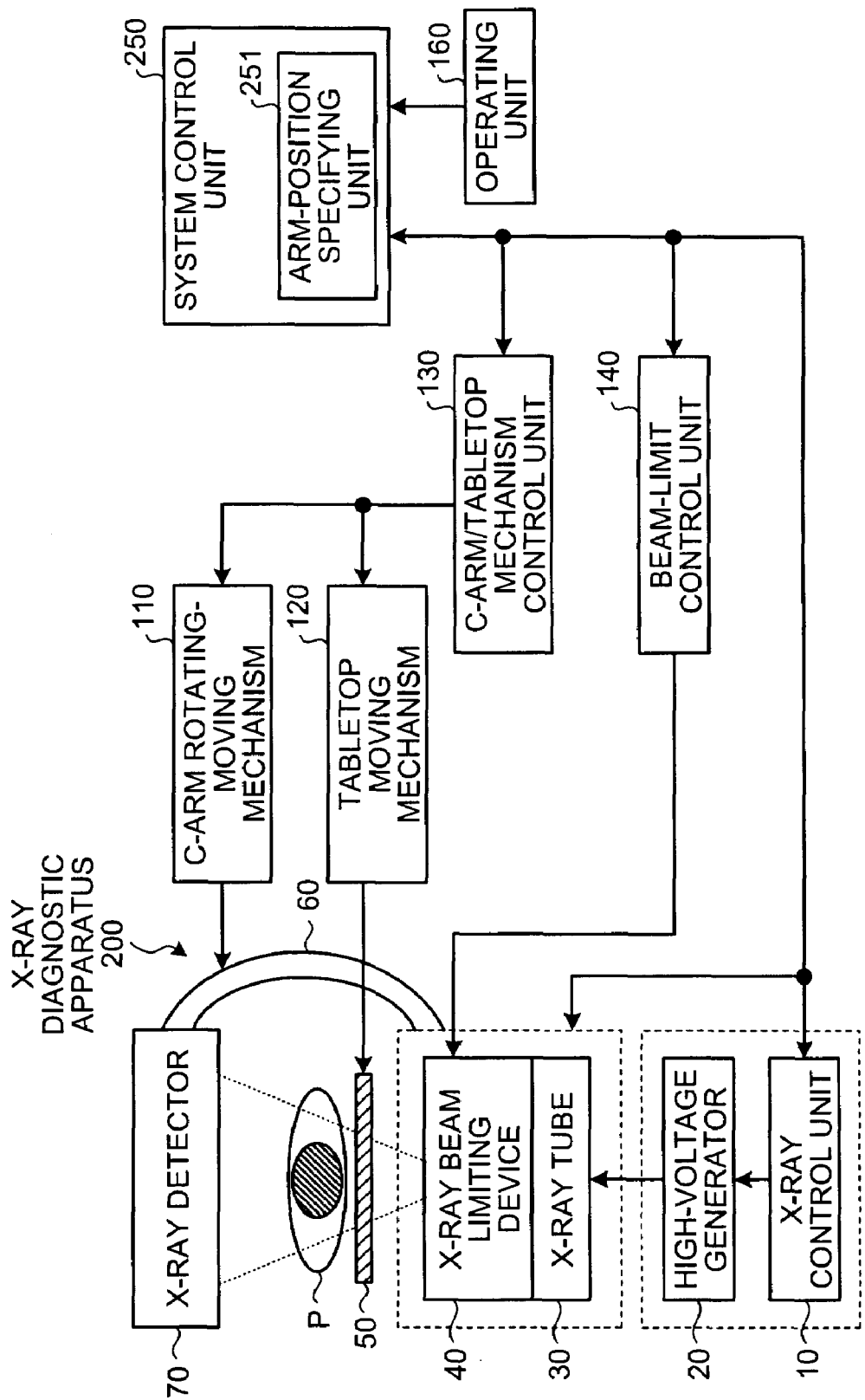

IF ONLY CLINICAL OBSERVATION ANGLE IS MATCHED WITH ANGLE PRIOR TO ROLLING, RADIATION FIELD IS DEVIATED FROM TARGET AREA

↓

DETERMINE TO WHICH POSITION TARGET POSITION SUBSEQUENT TO ROLLING COMES, AND MOVE ARM TO DETERMINED POSITION

60
C-ARM

MOVEMENT OF RAISING AND RECLINING TABLETOP

TABLETOP ROLLING MOVEMENT

X-RAY IMAGING APPARATUS

CROSS-REFERENCE TO RELATED APPLICATIONS

This application is based upon and claims the benefit of priority from the prior Japanese Patent Application No. 2006-340087, filed on Dec. 18, 2006; the entire contents of which are incorporated herein by reference.

BACKGROUND OF THE INVENTION

1. Field of the Invention

The present invention relates to an X-ray imaging apparatus, and particularly relates to setting of a radiation field of X-rays.

2. Description of the Related Art

In X-ray diagnostic apparatuses, in order to protect a patient, i.e., an object to be inspected, from unwanted radiation exposure, X-ray protection standards (for example, see JIS Z4701) are established, for example, such that a deviation between the boundary of an X-ray radiation field and the boundary covered by an X-ray detector should not exceed three percent of SID (source image distance, hereinafter abbreviated as SID, a distance between the focus of an X-ray tube and the X-ray detector).

For this reason, X-ray diagnostic apparatuses include a function, such as an auto-collimation function, to avoid unwanted radiation exposure. The auto-collimation function is a function such that, as shown in FIG. 14, a radiation field is narrowed by closing blades of an X-ray beam limiting device 40 automatically when an X-ray detector 70 moves away from an X-ray tube 30.

The auto-collimation function can prevent unwanted X-rays outside a beam receiving area of the X-ray detector 70, however, the auto-collimation function cannot prevent X-rays outside a ROI (Region of Interest) in the radiation field (for example, an edge part of the radiation field). Therefore, to restrict radiation of X-rays outside the ROI, an operator needs to operate the X-ray beam limiting device 40 manually and to narrow an X-ray beam.

Therefore, X-rays may be irradiated to a position deviated from the target position of the patient P when tabletop rolling for rotating a tabletop 50 around an axis in the head-tail direction of a patient P is carried out as shown in FIG. 15 in order to facilitate the operator's approach to the patient, and this leads to a problem that the patient is exposed to unwanted radiation.

SUMMARY OF THE INVENTION

According to one aspect of the present invention, an X-ray imaging apparatus includes a tabletop on which an object to be inspected lies; a tabletop rotating unit that rotates the tabletop around a predetermined axis; and a radiation-field control unit that controls a radiation field of X-rays irradiated onto the object in conjunction with a rotation of the tabletop rotated by the tabletop rotating unit.

BRIEF DESCRIPTION OF THE DRAWINGS

FIGS. 1A to 1E are schematic diagrams for explaining a concept of radiation-field control linked with tabletop-rolling according to a first embodiment of the present invention;

FIG. 2 is a functional block diagram of an X-ray imaging apparatus according to the first embodiment;

FIG. 6 is a functional block diagram of an X-ray imaging apparatus according to the second embodiment;

DETAILED DESCRIPTION OF THE INVENTION

Figure 3A:
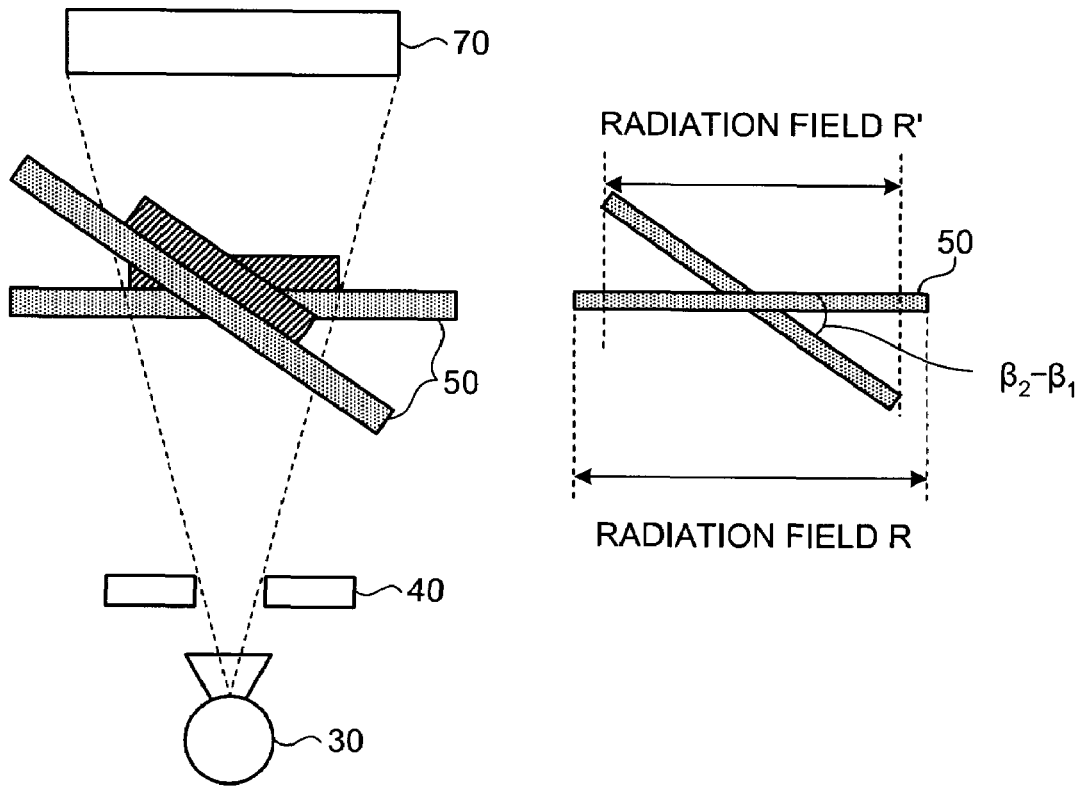
FIGS. 3A and 3B are schematic diagrams for explaining beam limit control of an X-ray beam limiting device linked with rolling of a tabletop.

Exemplary embodiments of the present invention will be explained below in detail with reference to the accompanying drawings.

First, a concept of radiation-field control linked with tabletop-rolling according to a first embodiment of the present invention is explained below. As shown in FIGS. 1A to 1E, the radiation-field control linked with tabletop-rolling according to the first embodiment prevents radiation of X-rays onto areas other than a target area by operating an X-ray beam limiting device 40 to limit an X-ray beam automatically when a tabletop 50 is rolling.

In other words, comparing with an image before the rolling as shown in FIG. 1B, if the radiation-field control linked with tabletop-rolling is not performed, X-rays are irradiated onto a wider area of a patient P, so that areas other than the target area are projected onto an image after the rolling (without limiting the radiation field) as shown in FIG. 1D. By contrast, if the radiation-field control linked with tabletop-rolling is performed (as shown in FIGS. 1A and 1C), only the target area is projected onto an image after the rolling (with limiting the radiation field) as shown in FIG. 1E.

Thus, narrowing the radiation field in conjunction with the rolling of the tabletop 50 can protect the patient P from unwanted radiation exposure, and can eliminate a possibility of halation caused by an area empty of object created in the radiation field.

Next, a configuration of an X-ray diagnostic apparatus 100 according to the first embodiment is explained below. As shown in FIG. 2, the X-ray diagnostic apparatus 100 includes an X-ray control unit 10, a high-voltage generator 20, an X-ray tube 30, the X-ray beam limiting device 40, a tabletop 50, a C-arm 60, an X-ray detector 70, a C-arm rotating-moving mechanism 110, a tabletop moving mechanism 120, a C-arm/tabletop mechanism control unit 130, a beam-limit control unit 140, a system control unit 150, and an operating unit 160.

The X-ray control unit 10 controls generation of X-rays by controlling generation of high voltage generated by the high-voltage generator 20. The high-voltage generator 20 supplies high voltage required for generation of X-rays to the X-ray tube 30. The X-ray tube 30 generates X-rays to be irradiated onto the patient P by using high voltage supplied from the high-voltage generator 20. The X-ray beam limiting device 40 shields X-rays generated by the X-ray tube 30. The tabletop 50 is a plate on which the patient P lies. The C-arm 60 supports the X-ray tube 30, the X-ray beam limiting device 40, and the X-ray detector 70 and the like. The X-ray detector 70 detects X-rays passed through the patient P.

The C-arm rotating-moving mechanism 110 rotates and moves the C-arm 60. The tabletop moving mechanism 120 rotates and moves the tabletop 50. The C-arm/tabletop mechanism control unit 130 controls the C-arm rotating-moving mechanism 110 and the tabletop moving mechanism 120, and causes the C-arm 60 and the tabletop 50 to rotate and move. The beam-limit control unit 140 controls the aperture of the diaphragm blades of the X-ray beam limiting device 40 thereby controlling the irradiation area of X-rays.

The system control unit 150 controls the whole of the X-ray diagnostic apparatus 100 by instructing the X-ray control unit 10, the C-arm/tabletop mechanism control unit 130, and the beam-limit control unit 140 based on an instruction from the operating unit 160. The system control unit 150 includes an aperture specifying unit 151 that specifies the aperture of the diaphragm blades for the beam-limit control unit 140 in conjunction with the rolling of the tabletop 50. The operating unit 160 is a console that receives an instruction from an operator, and transmits the instruction to the system control unit 150.

Next, beam limit control of the X-ray beam limiting device 40 linked with rolling of the tabletop 50 is explained below. FIG. 3A depicts a case where the center of the target area (the radiation field) matches with the center of the rolling, and FIG. 3B depicts a case where the center of the target area does not match with the center of the rolling.

As shown in FIG. 3A, when the center of the target area matches with the center of the rolling, a radiation field R' subsequent to tabletop rolling is expressed as R'=R×cos ($\beta_2$−$\beta_1$), where R is a radiation field prior to the tabletop rolling, $\beta_1$ is a tabletop rolling angle prior to the tabletop rolling, and $\beta_2$ is a tabletop rolling angle subsequent to the tabletop rolling. Accordingly, the aperture specifying unit 151 calculates R' from R, $\beta_1$, and $\beta_2$, calculates the aperture of the diaphragm blades to make the radiation field to be R', and specifies the calculated aperture of the diaphragm blades for the beam-limit control unit 140.

Figure 3B:
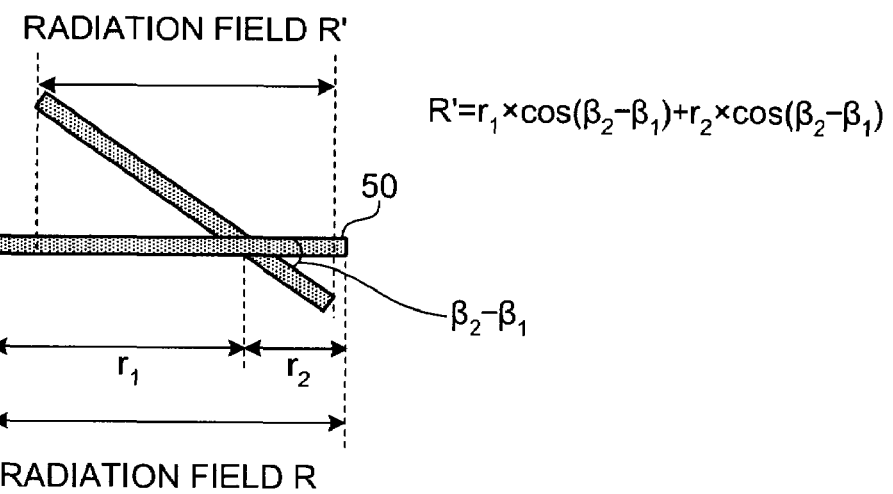

By contrast, when the center of the target area does not match with the center of the rolling, as shown in FIG. 3B, R' subsequent to tabletop rolling is expressed as R'=$r_1$×cos($\beta_2$−$\beta_1$)+$r_2$×cos ($\beta_2$−$\beta_1$), where $r_1$ and $r_2$ are each a distance between the center of the rolling and a boundary of the radiation field. Accordingly, the aperture specifying unit 151 calculates R' from $r_1$, $r_2$, $\beta_1$, and $\beta_2$.

Thus, the aperture specifying unit 151 calculates R' and the aperture of the diaphragm blades to make the radiation field to be R', and specifies the calculated aperture of the diaphragm blades for the beam-limit control unit 140. With this, the aperture of the diaphragm blades can be controlled in conjunction with the rolling of the tabletop 50, and the irradiation areas onto the patient P prior to and subsequent to the rolling can be matched.

Figure 4:
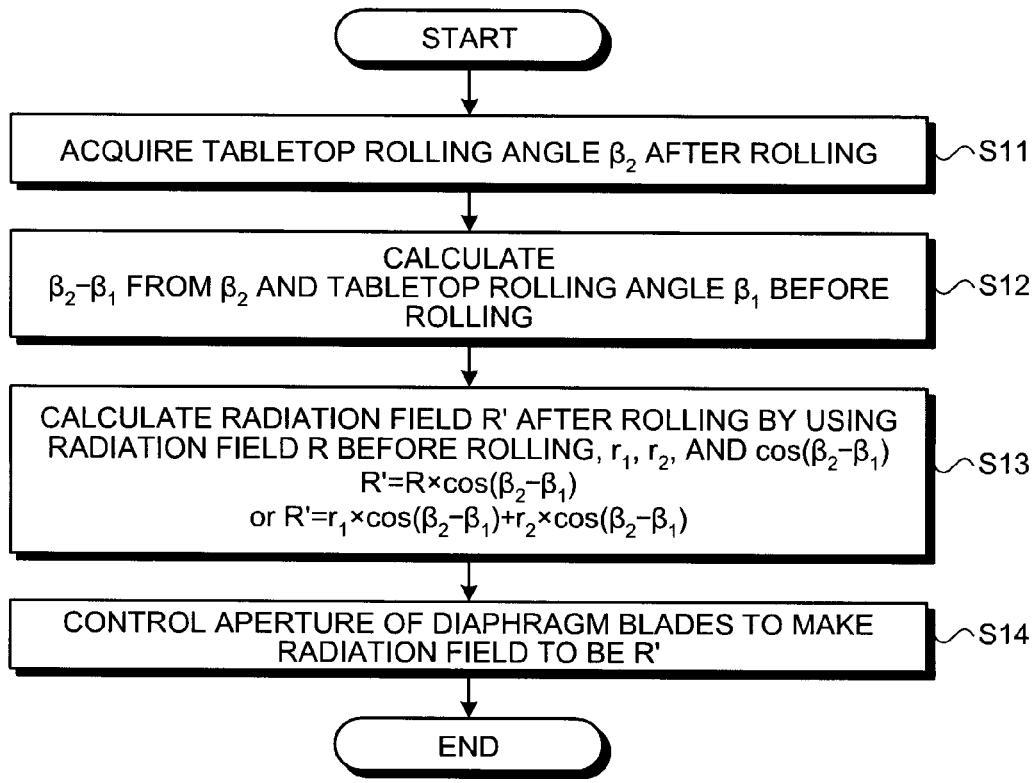
FIG. 4 is a flowchart of a procedure of the beam limit control of the X-ray beam limiting device linked with the rolling of the tabletop.

Next, a procedure of the beam limit control of the X-ray beam limiting device 40 linked with rolling of the tabletop 50 is explained below. FIG. 4 is a flowchart of a procedure of the beam limit control of the X-ray beam limiting device 40 linked with the rolling of the tabletop 50. In the following description, it is assumed that the aperture specifying unit 151 stores therein the tabletop rolling angle $\beta_1$ before rolling, the radiation field R before the rolling, and the distances $r_1$ and $r_2$ between the center of the rolling and the boundaries of the radiation field.

As shown in FIG. 4, in a procedure of the beam limit control, the aperture specifying unit 151 acquires the tabletop rolling angle $\beta_2$ after the rolling from the C-arm/tabletop mechanism control unit 130 (step S11). The C-arm/tabletop mechanism control unit 130 includes an angle sensor, and measures a tabletop rolling angle by using the angle sensor.

The aperture specifying unit 151 calculates $\beta_2$−$\beta_1$ from the acquired tabletop rolling angle $\beta_2$ and the stored tabletop rolling angle $\beta_1$ prior to the rolling (step S12). When the center of the target area matches with the center of the rolling, the aperture specifying unit 151 calculates the radiation field R' after the rolling, expressed as R'=R×cos ($\beta_2$−$\beta_1$), by using the radiation field R prior to the rolling, and cos ($\beta_2$−$\beta_1$). When the center of the target area does not match with the center of the rolling, the aperture specifying unit 151 calculates the radiation field R' subsequent to the rolling, expressed as $\beta_1$=$r_1$×cos ($\beta_2$−$\beta_1$)+$r_2$×cos ($\beta_2$−$\beta_1$), by using $r_1$, $r_2$, and cos ($\beta_2$−$\beta_1$) (step S13).

The aperture specifying unit 151 then calculates the aperture of the diaphragm blades to make the radiation field to be R', and specifies the calculated aperture of the diaphragm blades for the beam-limit control unit 140. The beam-limit control unit 140 then controls the aperture of the diaphragm blades to make the radiation field to be R' (step S14).

Thus, according to the first embodiment, the aperture specifying unit 151 calculates the aperture of the diaphragm blades to make the radiation field to be R', and specifies the calculated aperture of the diaphragm blades for the beam-limit control unit 140. The beam-limit control unit 140 then controls the aperture of the diaphragm blades to make the radiation field to be R'. Therefore, when the tabletop is rolling, irradiation of X-rays onto areas other than the target area can be prevented.

The first embodiment is explained above in the case where the X-ray beam limiting device 40 is controlled in conjunction with tabletop rolling, because it is assumed that the tabletop rolling is performed to facilitate an operator's approach to the patient P. On the other hand, there is a case where the operator wants to watch the target area from the same angle as prior to rolling when tabletop rolling is performed. According to a second embodiment of the present invention, an X-ray diagnostic apparatus is explained below in which the same area and direction of X-ray irradiation are to be kept through operations prior to and subsequent to tabletop rolling by positioning the C-arm 60 in conjunction with the tabletop rolling.

Figure 5:
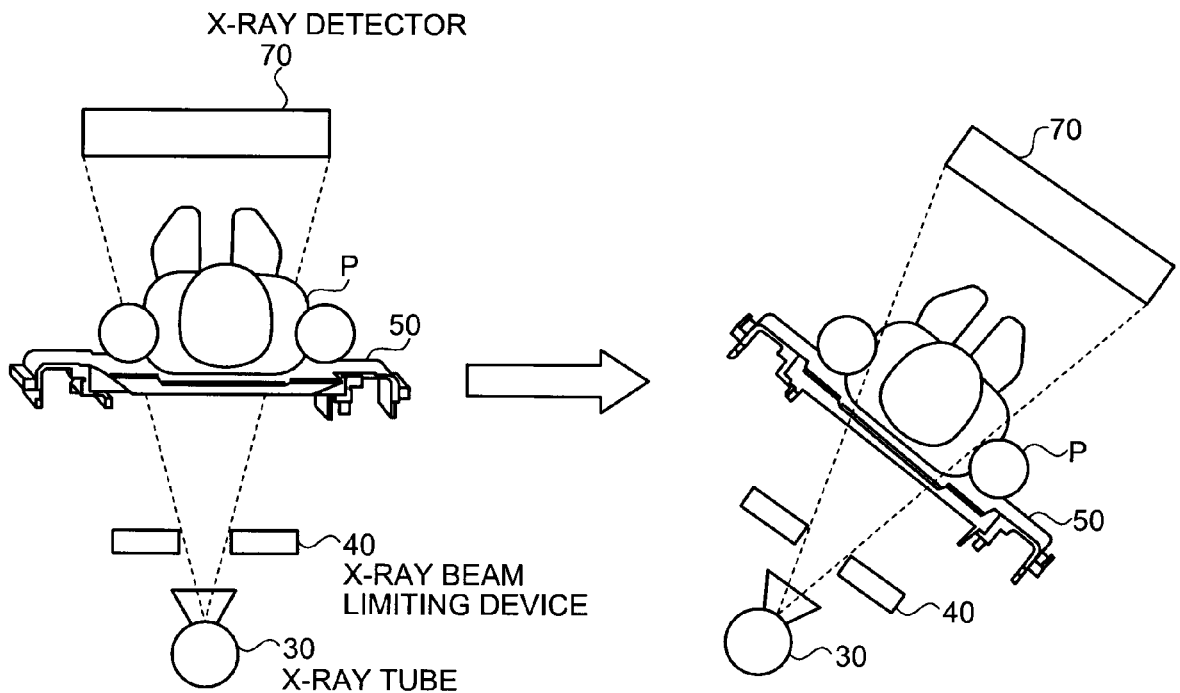
FIG. 5 is a schematic diagram for explaining a concept of radiation-field control linked with tabletop-rolling according to a second embodiment of the present invention.

A concept of radiation-field control linked with tabletop-rolling according to the second embodiment is explained below. As shown in FIG. 5, when the tabletop 50 is rolling, the radiation-field control linked with tabletop-rolling according to the second embodiment causes the X-ray tube 30 to rotate similarly to the tabletop 50.

Thus, the radiation-field control linked with tabletop-rolling according to the second embodiment can prevent irradiation of X-rays onto areas other than a target area, and also an operator can watch the target area from the same direction as before the rolling, by rotating the X-ray tube 30 similarly to the tabletop 50.

Next, a configuration of an X-ray diagnostic apparatus 200 according to the second embodiment is explained below. For convenience of explanations, functional units that work similarly to those shown in FIG. 2 are assigned with the same reference numerals, and detailed explanations of them are omitted.

As shown in FIG. 6, the X-ray diagnostic apparatus 200 includes a system control unit 250 instead of the system control unit 150 included in the X-ray diagnostic apparatus 100 shown in FIG. 2. Similarly to the system control unit 150, the system control unit 250 controls the whole of the X-ray diagnostic apparatus 200 by instructing the X-ray control unit 10, the C-arm/tabletop mechanism control unit 130, and the beam-limit control unit 140, based on an instruction from the operating unit 160. However, the system control unit 250 includes an arm-position specifying unit 251 instead of the aperture specifying unit 151.

The arm-position specifying unit 251 specifies a position of the C-arm 60 for the C-arm/tabletop mechanism control unit 130 so as not to change an area onto which X-rays are irradiated to the patient P from before to after rolling, when the tabletop 50 is rolling. The C-arm/tabletop mechanism control unit 130 controls the C-arm 60 to be positioned at a point specified by the arm-position specifying unit 251.

Figure 7A:
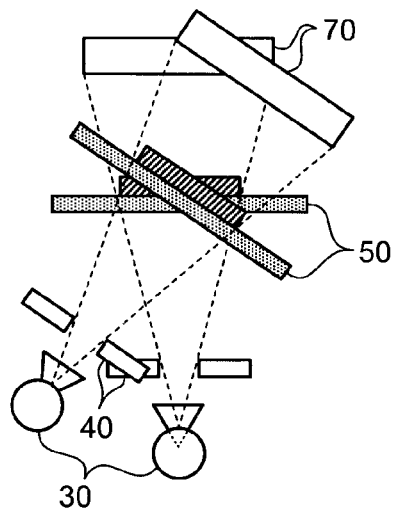
FIGS. 7A to 7C are schematic diagrams for explaining positioning of a C-arm linked with rolling of a tabletop.

Positioning of the C-arm 60 linked with rolling of the tabletop 50 is explained below. FIG. 7A depicts a case where the center of the target area matches with the rolling axis, and FIG. 7B depicts a case where the center of the target area does not match with the rolling axis.

As shown in FIG. 7A, when the center of the target area matches with the rolling axis, the arm-position specifying unit 251 positions the C-arm 60 such that the X-ray tube 30 and the X-ray detector 70 are rotated to the same angle as the rolling angle of the tabletop 50. Details of the positioning of the C-arm 60 will be described later.

Figure 7B:
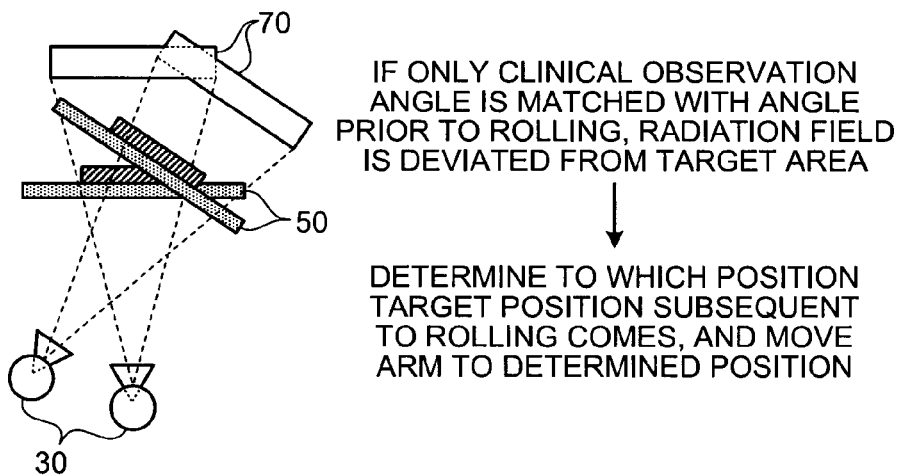

By contrast, when the center of the target area does not match with the rolling axis, as shown in FIG. 7B, if the X-ray tube 30 and the X-ray detector 70 are simply rotated to the same angle as the rolling angle of the tabletop 50, namely, only a clinical observation angle is matched with the angle prior to the rolling, the target area is deviated from the radiation field.

Figure 7C:
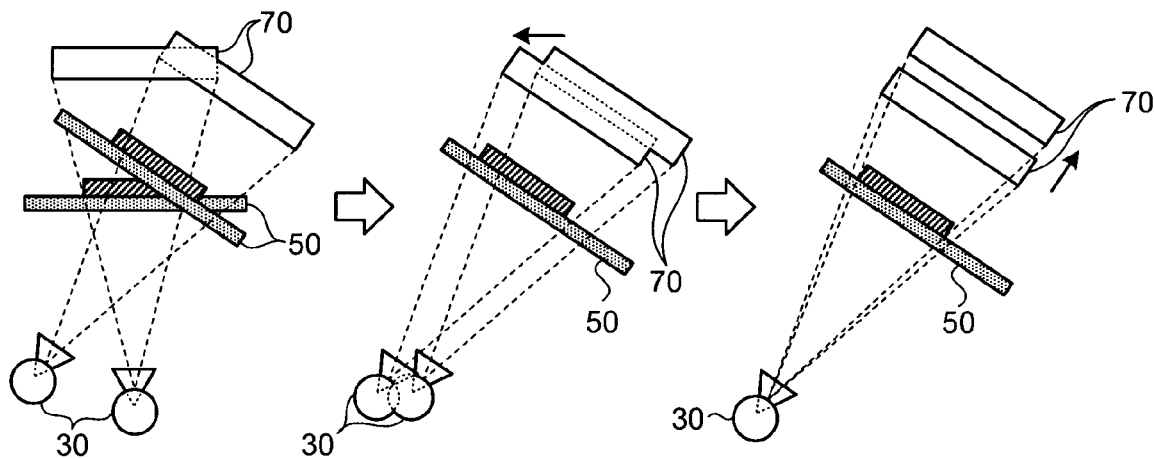

For this reason, the arm-position specifying unit 251 positions the C-arm 60, as shown in FIG. 7C, to cancel a positional deviation of the radiation field from the target area by aligning longitudinal and lateral position of the C-arm 60. However, if the C-arm 60 is positioned in this way, the distance from the focus of the X-ray tube 30 to the target position and the distance from the target position to the X-ray detector 70 are changed, so that a deviation in width arises between the target area and the radiation field. Therefore, the arm-position specifying unit 251 further adjusts the distance SID, from the focus of the X-ray tube 30 to the X-ray detector 70, to match the width of the target area and that of the radiation field.

In this case, the operator's approach to the patient P has priority, so that an adjustment for deviation is performed by the C-arm 60, meanwhile the tabletop 50 is only rolling. However, adjustment for deviation can be performed by the tabletop 50 and the C-arm 60 in cooperation. For example, if the height of the tabletop 50 can be changed without problem, the distance from the focus of the X-ray tube 30 to the target position and the distance from the target position to the X-ray detector 70 can be kept constant by changing the height of the tabletop 50 in conjunction with the tabletop rolling.

Figure 8:
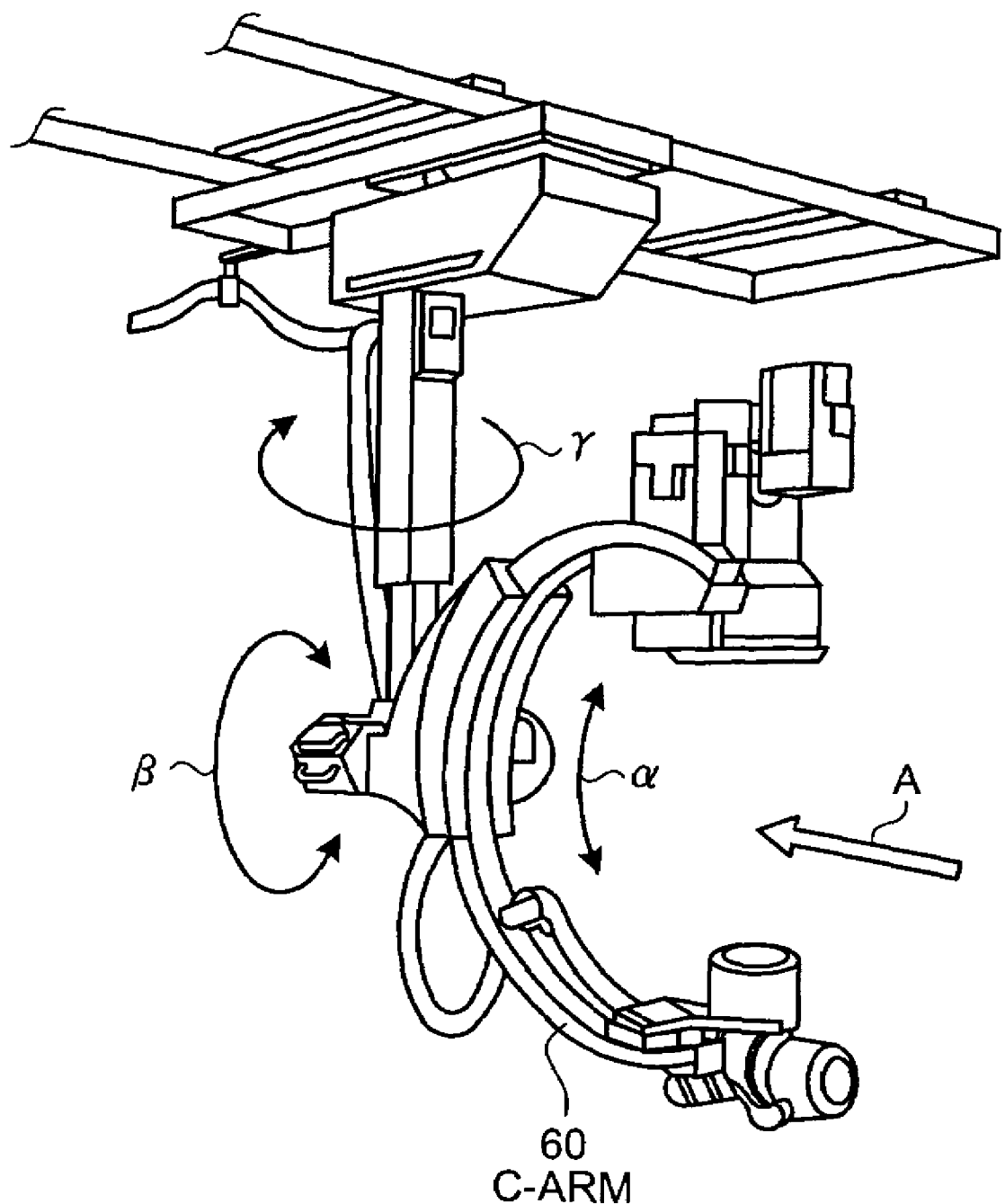
FIG. 8 is a perspective view of the C-arm.
Figure 9A:
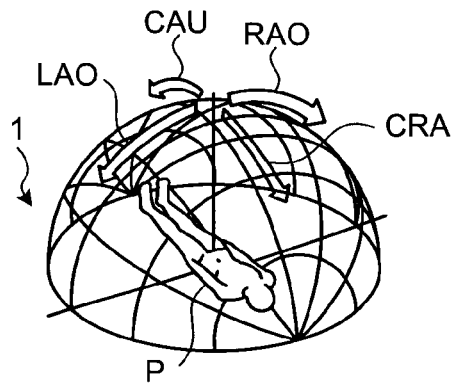
FIGS. 9A to 9C are schematic diagrams for explaining positioning of the C-arm.
Figure 9B:
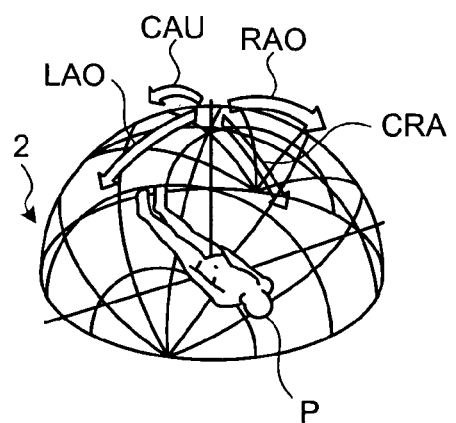

Next, positioning of the C-arm 60 such that the X-ray tube 30 and the X-ray detector 70 are rotated to the same angle as the rolling angle of the tabletop 50 is explained with reference to FIGS. 8, 9A, 9B, and 9C. FIG. 8 is a perspective view of the C-arm 60. The head of the patient P is usually inserted into an X-ray diagnostic apparatus from the direction of an arrow A shown in FIG. 8 (where this direction is assumed to be zero degree for angle $\gamma$). While the angle in the direction $\gamma$ is fixed, the C-arm 60 is rotated in a direction $\alpha$ and in a direction $\beta$ individually, so that orbits 1 around the patient P as shown in FIG. 9A are obtained. In other words, the C-arm 60 can be moved to directions CRA and CAU by rotating the C-arm 60 in the direction $\alpha$, and the C-arm 60 can be moved to directions LAO and RAO by rotating the C-arm 60 in the direction $\beta$.

However, in practice, the patient P is not always radiographed in the direction of the arrow A shown in FIG. 8 due to a problem of interference from peripheral equipments during a clinical observation or a requirement for a clinical observation. There is a case where the patient P is radiographed in an oblique direction (a direction at a degree other than zero in the angle $\gamma$). In such case, a radiographic direction for the patient P differs from the direction in the case shown in FIG. 9A, and orbits are obtained as shown as orbits 2 in FIG. 9B, for example. In other words, if the rotation in the direction $\alpha$ and the rotation in the direction $\beta$ are only individually controlled, orbits in the directions LAO, RAO, CAU, and CRA shown in FIG. 9A cannot be obtained.

Figure 9C:
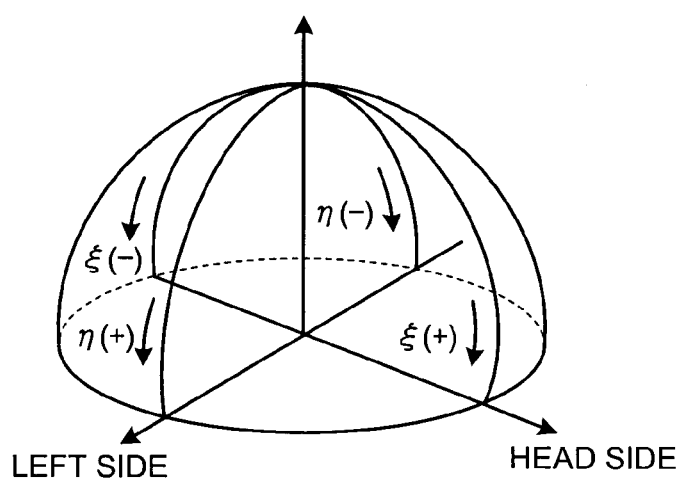

Therefore, it is assumed that a head side and a left side of the patient P are determined as shown in FIG. 9C, and $\xi(+)$ is CRA, $\xi(-)$ is CAU, $\eta(+)$ is LAO, and $\eta(-)$ is RAO. When the tabletop 50 is rolled from the rolling angle $\beta_1$ to $\beta_2$, the target position is deemed to be rotated by $(\beta_2-\beta_1)$ in the direction LAO/RAO, so that the arm-position specifying unit 251 positions the C-arm 60 at an arm angle (LAO/RAO $\eta_1+(\beta_2-\beta_1)$, CRA/CAU $\xi_1$), where (LAO/RAO $\eta_1$, CRA/CAU $\xi_1$) is a clinical observation angle prior to the rolling. The control of positioning an arm at a clinical observation angle of LAO/RAO and CRA/CAU is described in JP-A H8-84723 (KOKAI).

Figure 10:
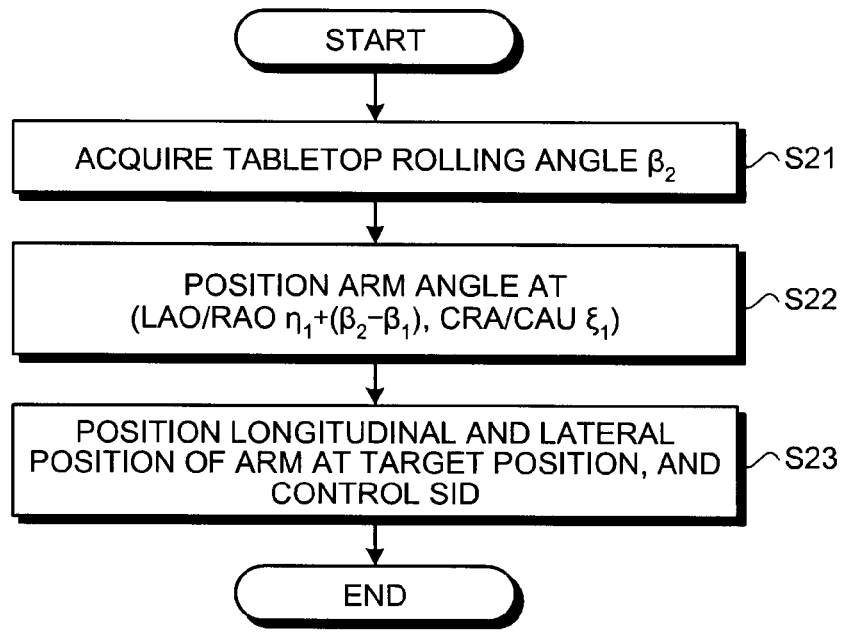
FIG. 10 is a flowchart of a procedure of positioning control of the C-arm linked with the rolling of the tabletop.

Next, a procedure of positioning control of the C-arm 60 linked with rolling of the tabletop 50 is explained below. FIG. 10 is a flowchart of a procedure of positioning control of the C-arm 60 linked with the rolling of the tabletop 50. It is assumed that the arm-position specifying unit 251 stores therein the clinical observation angle prior to the rolling (LAO/RAO $\eta_1$, CRA/CAU $\xi_1$), and the tabletop rolling angle $\beta_1$.

As shown in FIG. 10, in the procedure of the positioning control, the arm-position specifying unit 251 acquires the tabletop rolling angle $\beta_2$ subsequent to the rolling from the C-arm/tabletop mechanism control unit 130 (step S21).

The arm-position specifying unit 251 instructs the C-arm/tabletop mechanism control unit 130 to position the arm angle at (LAO/RAO $\eta_1+(\beta_2-\beta_1)$, CRA/CAU $\xi_1$) by using the stored clinical observation angle (LAO/RAO $\eta_1$, CRA/CAU $\xi_1$), the tabletop rolling angle $\beta_1$, and the acquired angle $\beta_2$ and the C-arm/tabletop mechanism control unit 130 controls the arm angle to be positioned at (LAO/RAO $\eta_1+(\beta_2-\beta_1)$, CRA/CAU $\xi_i$) (step S22).

The arm-position specifying unit 251 further instructs the C-arm/tabletop mechanism control unit 130 to position the longitudinal and lateral position of the C-arm 60 to the target position, and also to control SID in conjunction with the rolling in a manner such that the width of the target area matches with the width of the radiation field. The C-arm/tabletop mechanism control unit 130 then controls positioning of the C-arm 60 in accordance with the instruction from the arm-position specifying unit 251, and controls SID in conjunction with the rolling (step S23).

As mentioned above, according to the second embodiment, the arm-position specifying unit 251 performs positioning of the C-arm 60 linked with rolling of the tabletop 50 so as to maintain an area onto which X-rays are irradiated and a direction of the X-ray constant from before to after rolling of the tabletop, and the C-arm/tabletop mechanism control unit 130 controls to position the C-arm 60 according to an instruction from the arm-position specifying unit 251. Therefore, irradiation of X-rays onto areas other than the target area can be prevented when the tabletop is rolling.

Next, modes of the radiation-field control linked with tabletop-rolling according to the first and second embodiments are explained below. The X-ray diagnostic apparatuses 100 and 200 are configured to perform the radiation-field control linked with tabletop-rolling in two modes, namely, a real-time mode, and a step-by-step mode.

In the real-time mode, the X-ray diagnostic apparatuses 100 and 200 perform the radiation field control while performing the tabletop rolling. Precisely, according to the real-time mode, the X-ray diagnostic apparatus 100 controls the aperture of the diaphragm blades while performing the tabletop rolling, and the X-ray diagnostic apparatus 200 controls the position of the C-arm 60 while performing the tabletop rolling.

In the step-by-step mode, the X-ray diagnostic apparatuses 100 and 200 perform the radiation field control after the tabletop rolling is finished. Precisely, according to the step-by-step method, the X-ray diagnostic apparatus 100 receives an instruction from the operator after the tabletop rolling is finished, and then controls the aperture of the diaphragm blades to make the radiation field to be equal to the radiation field prior to the tabletop rolling. The X-ray diagnostic apparatus 200 receives an instruction from the operator after the tabletop rolling is finished, and then controls the position of the C-arm 60 to make the radiation field to be equal to the radiation field prior to the tabletop rolling.

The operator can designate either the real-time mode or the step-by-step mode of the radiation-field control linked with tabletop-rolling via the operating unit 160. Specifically, if the operating unit 160 includes an operation panel and a graphical user interface (GUI) on a display device, the operator can determine whether to perform the radiation-field control linked with tabletop-rolling, and can select either the real-time mode or the step-by-step mode if determined to perform, by using a switch on the operation panel or a selection button on the GUI on the display device. If the step-by-step mode is selected, the operator can give an instruction to start the radiation-field control linked with tabletop-rolling by using a switch on the operation panel or a selection button on the GUI on the display device after finishing the tabletop-rolling.

Figure 11:
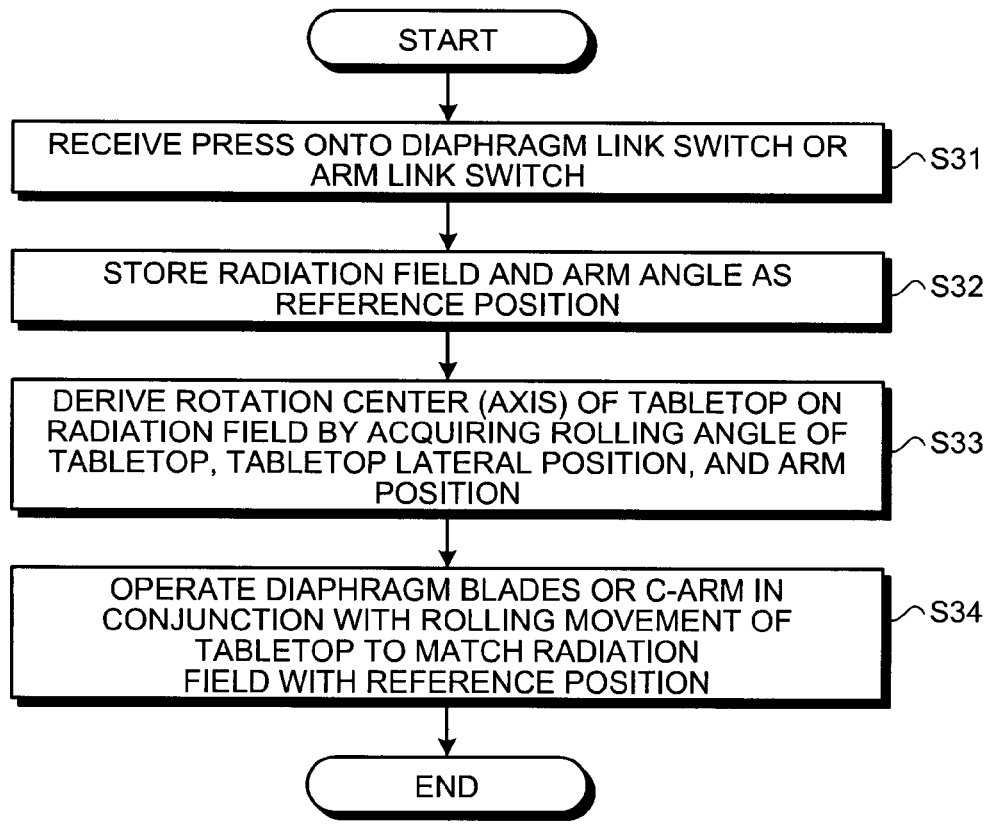
FIG. 11 is a flowchart of a procedure of the radiation-field control linked with tabletop-rolling performed in the real-time mode.

A procedure of the radiation-field control linked with tabletop-rolling performed in the real-time mode is shown in FIG. 11. As shown in FIG. 11, in the real-time mode, the system control unit 150 or 250 receives a press onto a diaphragm link switch or a press onto an arm link switch (step S31). The diaphragm link switch is configured to be pressed by the operator when controlling the aperture of the diaphragm blades in real time in a linked manner. The arm link switch is configured to be pressed by the operator when controlling the position of the C-arm 60 in real time in a linked manner.

The system control unit 150 or 250 stores therein the radiation field and the arm angle prior to the tabletop rolling as a reference position (step S32), and derives the rotation center (axis) of the tabletop 50 on the radiation field by acquiring the rolling angle of the tabletop 50, the tabletop lateral position, and the arm position (step S33). The system control unit 150 or 250 operates the diaphragm blades or the C-arm 60 in conjunction with the rolling of the tabletop 50 to match the radiation field with the reference position (step S34).

Thus, the radiation-field control linked with tabletop-rolling can be performed in real time, by operating the diaphragm blades or the C-arm 60 in conjunction with the rolling of the tabletop 50 to match the radiation field with the reference position.

Figure 12:
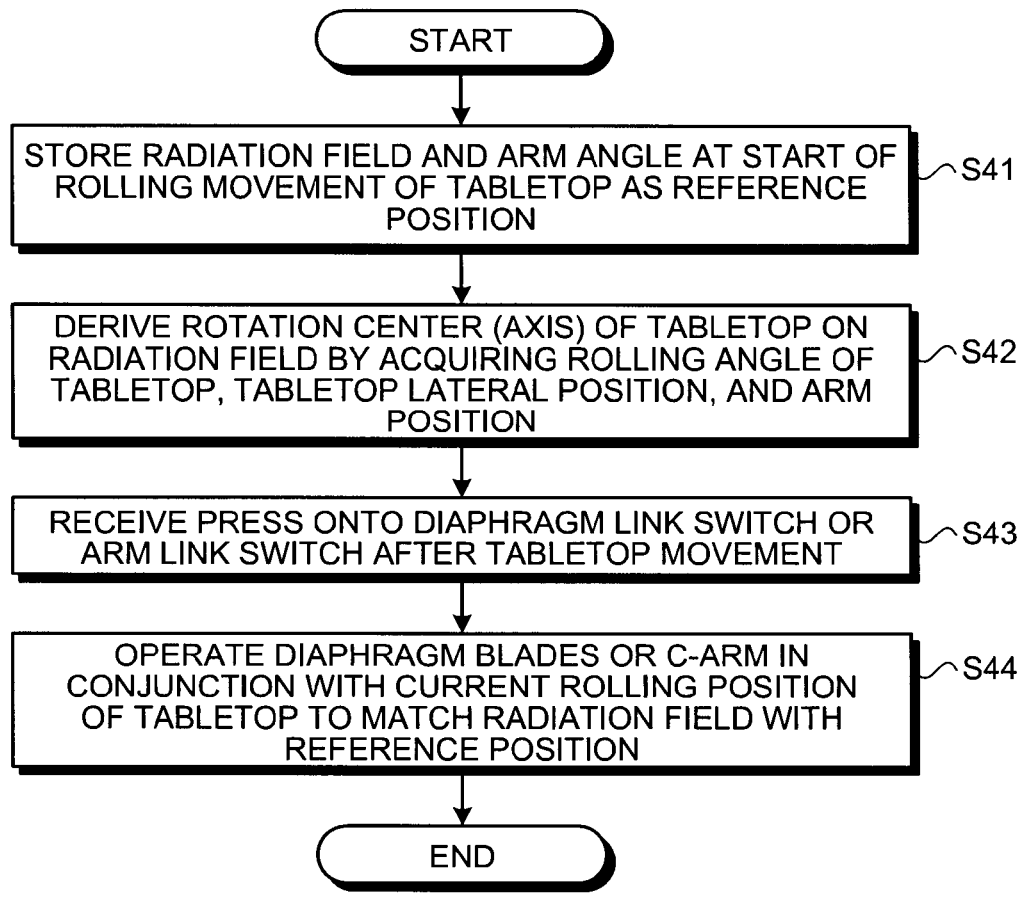
FIG. 12 is a flowchart of a procedure of the radiation-field control linked with tabletop-rolling performed in the step-by-step mode.

A procedure of the radiation-field control linked with tabletop-rolling performed in the step-by-step mode is shown in FIG. 12. As shown in FIG. 12, in the step-by-step mode, the system control unit 150 or 250 stores therein the radiation field and the arm angle at the moment of starting rolling movement of the tabletop 50 as a reference position (step S41).

The system control unit 150 or 250 then derives the rotation center (axis) of the tabletop 50 on the radiation field by acquiring the rolling angle of the tabletop 50, the tabletop lateral position, and the arm position (step S42). After the tabletop movement is finished, the system control unit 150 or 250 receives a press onto the diaphragm link switch or a press onto the arm link switch (step S43), and then operates the diaphragm blades or the C-arm 60 in accordance with the current rolling position of the tabletop 50 to match the radiation field with the reference position (step S44).

Thus, the radiation-field control linked with tabletop-rolling can also be performed by operating the diaphragm blades or the C-arm 60 to match the radiation field with the reference position for the position of the tabletop 50 after the tabletop movement is finished.

Although the X-ray diagnostic apparatuses 100 and 200 that include the C-arm 60 are explained in the first and second embodiments, the present invention is not limited to this. The present invention can be similarly applied to an X-ray diagnostic apparatus that includes an other arm, for example, an Ω-arm, or an X-ray diagnostic apparatus that includes an other arm in addition to the C-arm 60.

The first embodiment is explained in the case where the aperture specifying unit 151 in the system control unit 150 specifies the aperture of the diaphragm of the X-ray beam limiting device 40 in conjunction with the rolling of the tabletop 50, and the second embodiment is explained in the case where the arm-position specifying unit 251 in the system control unit 250 specifies the position of the C-arm 60 in conjunction with the rolling of the tabletop 50. However, a system control unit can be configured to include the aperture specifying unit 151 and the arm-position specifying unit 251, and to allow an operator to determine which function to be activated by using a switch on the operation panel or a selection button on the GUI on the display device. Alternatively, the beam-limit control unit 140 can be configured to include the function of the aperture specifying unit 151, and the C-arm/tabletop mechanism control unit 130 can be configured to include the function of the arm-position specifying unit 251.

Figure 13:
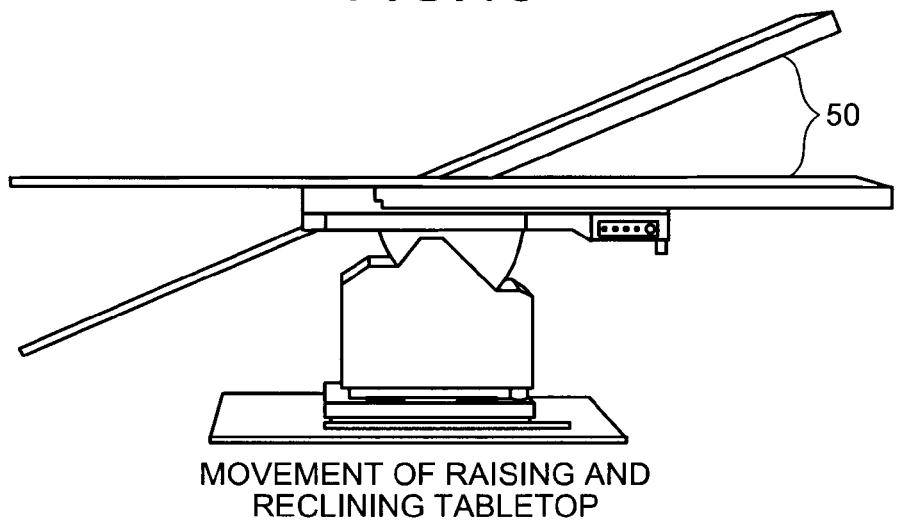
FIG. 13 is a schematic diagram for explaining a movement of raising and reclining the tabletop.
Figure 14:
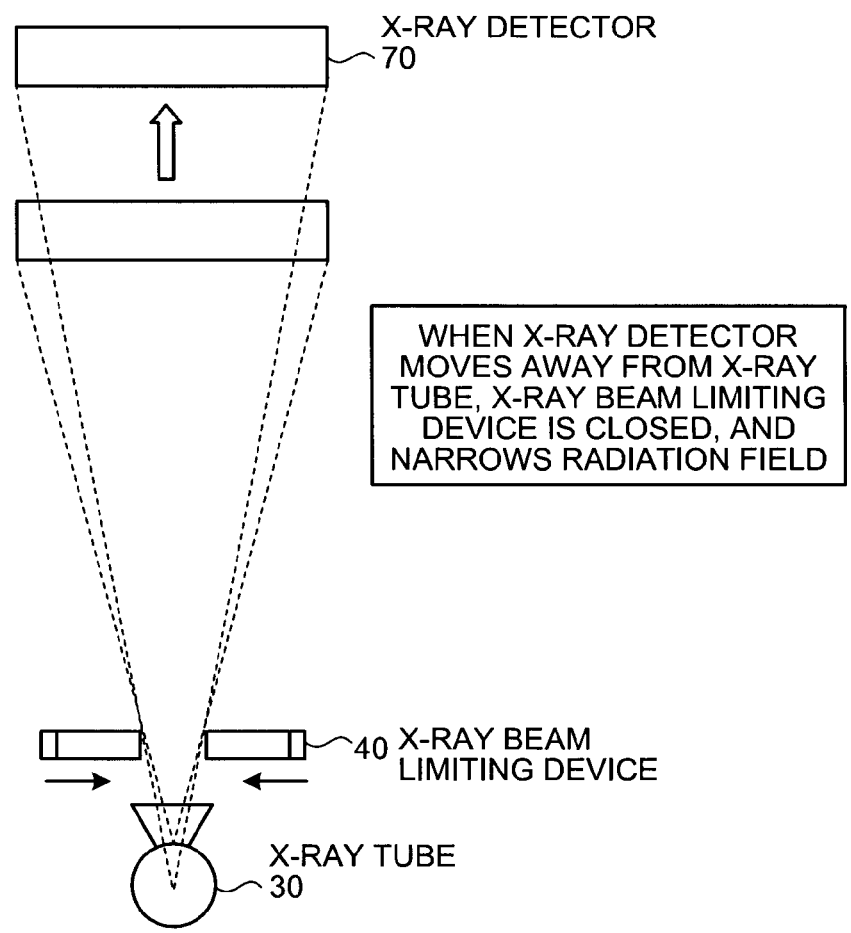
FIG. 14 is a schematic diagram for explaining a function of auto-collimation according to a related art.
Figure 15:
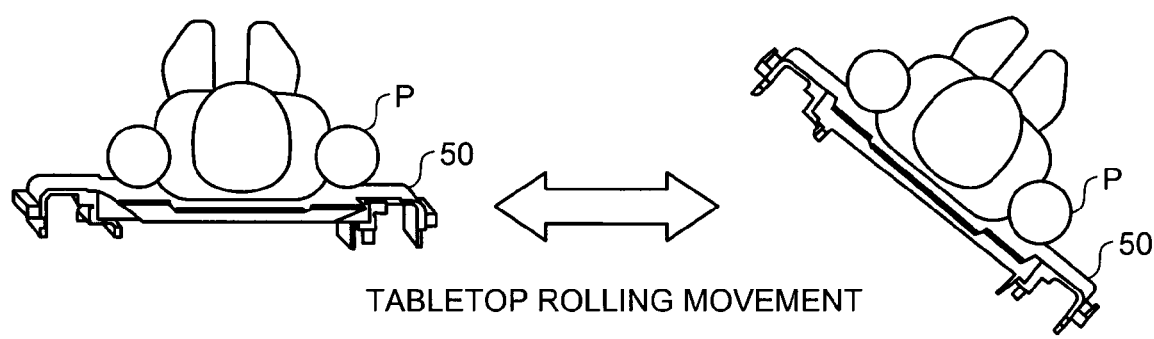
FIG. 15 is a schematic diagram for explaining movements of tabletop rolling.

Although the first and second embodiments are explained in the case where the radiation field is controlled in conjunction with the rolling movement of the tabletop 50, the present invention is not limited to this. As shown in FIG. 13, the present invention can be similarly applied to a case where the radiation field is controlled in conjunction with a movement of raising and reclining the tabletop that inclines upward inclination (an attitude with head up and feet down) or downward inclination (an attitude with head down and feet up) with respect to a support unit for the tabletop 50 as an axis. The movement of raising and reclining the tabletop is performed in manipulations for carbon dioxide angiography, for example.

Although the X-ray diagnostic apparatuses are explained in the first and second embodiments, the present invention is not limited to this. The present invention can be similarly applied to an X-ray imaging apparatus that takes a radiograph of an object to be inspected by irradiating X-rays onto the object on a tabletop.

As mentioned above, the X-ray imaging apparatus according to the embodiments of the present invention is effective in a case where the tabletop is rolling, and especially, is preferably applied to a case where unwanted radiation exposure must be suppressed as far as possible.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray imaging apparatus comprising:
   a tabletop on which an object to be inspected lies;
   a tabletop rotating unit that rotates the tabletop around a predetermined axis; and
   a radiation-field control unit that controls a radiation field of X-rays irradiated onto the object in conjunction with a rotation of the tabletop rotated by the tabletop rotating unit, wherein the radiation-field control unit controls a position of an arm that supports an X-ray tube and an X-ray detector in conjunction with the rotation of the tabletop.

2. The apparatus according to claim 1, wherein the radiation-field control unit controls a distance between the X-ray tube and the X-ray detector in conjunction with the rotation of the tabletop.

3. The apparatus according to claim 2, wherein the radiation-field control unit controls the radiation field of X-rays in conjunction with the rotation of the tabletop in real time during the rotation of the tabletop.

4. The apparatus according to claim 2, wherein the radiation-field control unit controls the radiation field in conjunction with the rotation of the tabletop based on a position of the tabletop after the rotation.

5. The apparatus according to claim 2, further comprising a link-control-instruction receiving unit that receives from an operator an instruction whether the radiation-field control unit controls the radiation field.

6. The apparatus according to claim 1, wherein the radiation-field control unit controls the radiation field of X-rays in conjunction with the rotation of the tabletop in real time during the rotation of the tabletop.

7. The apparatus according to claim 1, wherein the radiation-field control unit controls the radiation field in conjunction with the rotation of the tabletop based on a position of the tabletop after the rotation.

8. The apparatus according to claim 1, further comprising a link-control-instruction receiving unit that receives from an operator an instruction whether the radiation-field control unit controls the radiation field.

* * * * *